United States Patent [19]

Larach

[11] 3,984,683
[45] Oct. 5, 1976

[54] APPARATUS AND METHOD FOR ANALYZING BIOLOGICAL CELLS FOR MALIGNANCY

[75] Inventor: Simon Larach, Princeton, N.J.
[73] Assignee: RCA Corporation, New York, N.Y.
[22] Filed: May 27, 1975
[21] Appl. No.: 581,043

[52] U.S. Cl. .............................. 250/310; 250/306; 250/307; 128/2 A
[51] Int. Cl.² ........................................ H01J 37/06
[58] Field of Search ........... 250/305, 306, 307, 310, 250/311; 128/2 A, 2 R

[56] References Cited
UNITED STATES PATENTS
3,761,709  9/1973  Hasegawa et al. ................. 250/311

OTHER PUBLICATIONS
"The X-Ray Scanning Microanalyzer" Duncumb, British Journal of Applied Physics, vol. 10, Sept. 1959, pp. 420-427.
"Electron Microscope Imaging of Biological Structures Using Light Phase Contrast" Unwin- Micron 1971, No. 4, pp. 406-410.

Primary Examiner—Alfred E. Smith
Assistant Examiner—Bruce C. Anderson
Attorney, Agent, or Firm—Edward J. Norton; Robert L. Troike

[57] ABSTRACT

A specimen containing biological cells is exposed to an electron beam. The secondary electrons emitted from the specimen are measured. Specimens with and without malignancy exhibit differences in magnitude of charging under an electron beam and differences in secondary electron energy distributions.

9 Claims, 3 Drawing Figures

APPARATUS AND METHOD FOR ANALYZING BIOLOGICAL CELLS FOR MALIGNANCY

BACKGROUND OF THE INVENTION

This invention relates to an apparatus and method for analyzing biological cells for malignancy and more particularly to an apparatus and method for cytologic diagnosis of vaginal cancers.

The Papanicolaou [Pap] smear test for cytologic diagnosis of vaginal cancer has become a standard medical practice. In this test samples are taken, stained (dye applied) and examined by a technician under a microscope. The technician must not only read the sample carefully but also must interpret the results. Many technicians spend many hours each day reading and interpreting the results of such tests. This procedure has produced numerous errors in screening. A more objective, quantitative method of cytopathologic diagnosis is therefore needed.

BRIEF DESCRIPTION OF INVENTION

Briefly, a method and apparatus for analyzing specimens of biological cells is described wherein the specimens are exposed to an electron beam and the number of secondary electrons emitted are measured to determine malignancy.

DETAILED DESCRIPTION OF INVENTION

A detailed description follows in conjunction with the drawing wherein.

Before discussing the method and apparatus of the present invention, it is necessary to discuss some preliminary considerations including certain characteristics of a specimen to be examined.

E. J. Ambrose has shown that decreased molecular order within a malignant cell constitutes one of the most general changes observed in malignancy. (See E. J. Ambrose, Abstr. Vth International Liquid Crystal Conference Stockholm, 1974, page 189.) It is known that the secondary emission properties of non-biological materials depend on the nature of the molecular structure of the surface region. It is taught herein that the secondary emission properties of biological cells will describe the nature of the molecular structure and will enable one to distinguish between normal and malignant cells.

Figure 1:
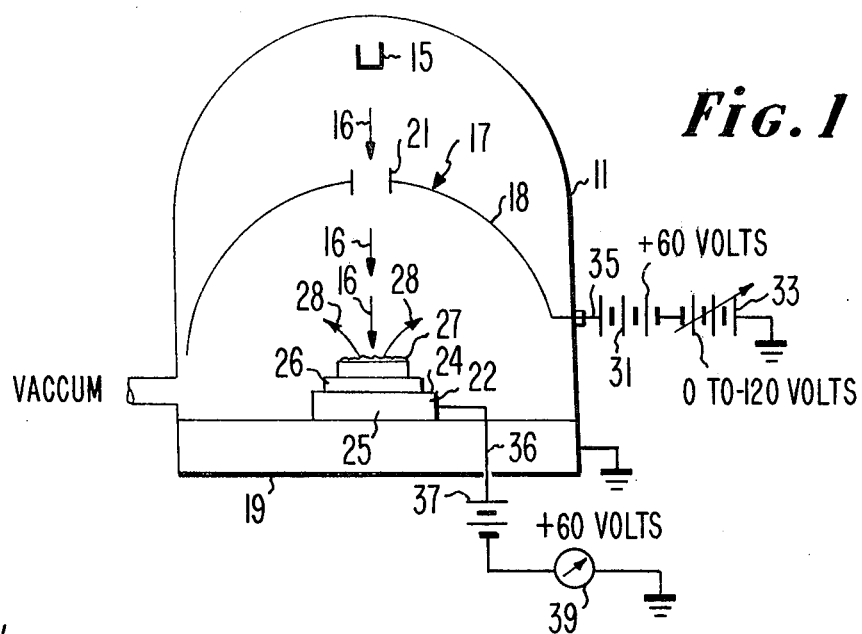
FIG. 1 is a schematic diagram of apparatus used to measure secondary electron emission properties.

Referring now to FIG. 1, there is shown a chamber 11 evacuable to a low pressure by standard facilities, not shown. A conductive target plate 22, a standard electron gun 15, and an emitted electron retardation system 17 are contained in the chamber 11. The electron gun 15 is so positioned that a beam of electrons may be directed at the target plate 22. The acceleration potential of the electron beam from gun 15 is, for example, between 50 volts and 10,000 volts. Typically, an acceleration potential of 2000 volts is used. The potential of the beam is of sufficient magnitude to minimize noise due to the mixing of the reflected primary electrons with secondary emission electrons and is less than that required to penetrate the specimen completely. The electron gun 15 is shown generally and may include standard facilities such as a cathode, an anode, electron optics, deflection plates, etc. not shown. The target plate 22 is of conductive material and may be rotatably mounted. On the top surface 24 of plate 22 is the specimen 27 on a glass slide 26. The specimen 27 may be a sample of biological cells as taken for a typical "Pap" smear test. The sample or specimen 27 is placed unstained on the glass slide 26. The glass slide 26 is mounted to the top surface 24 of the target plate with the specimen toward the electron gun 15.

The electron retardation system 17 includes a hemispherical conductive dome 18 with an open concave side facing the target plate 22. Mounted through the dome 18 on a radius thereof is a standard drift tube 21 through which the electron beam (indicated by arrows 16) passes in traveling to the target plate 22. The drift tube 21 merely prevents the electron beam from being adversely affected by varying potentials on the various elements of the electron retardation system 17. A first D.C. bias voltage source 31 of +60 volts is provided by a first battery. This source 31 is connected to the dome 18 via conductor 35. Conductor 35 passes through and is insulated from the wall of chamber 11. In series with this first battery source 31 and ground is a variable, reverse polarized bucking battery source 33. The variable source 33 is capable of providing in this example from zero to −120 volts. The conductive dome 18 is therefore coupled to a source of net potential of from +60 volts to −60 volts. The dome 18 is mounted in an insulative manner from the walls of chamber 11 and the target plate 22. The target plate 22 is mounted in an insulative manner from the base 19 and walls of the chamber 11. A positive D.C. potential source 37 is coupled to the target plate via conductor 36. This source 37 is about +60 volts and is grounded in series with an electrometer 39 or other current sensor. The metal target plate 22 so biased functions as the collector for the secondary emission electrons. The apparatus described above operates by using the retardation potential as a means for measuring secondary emissions.

In the operation of the apparatus, primary electron beams are generated by the electron gun 15, pass through the drift tube 21 and impinge on the specimen 27. The secondary electrons emitted as indicated by the arrows 28 in FIG. 1 disperse away from the material. The retardation potential provided at dome 18 by the voltage at the variable bias source 33 controls the amount of secondary electrons reflected away from the dome 18 toward the target plate 22. The secondary electrons are collected at the plate 22. The secondary electron current through the electrometer 39 is measured both with the glass slide 26 only inserted on the target plate 22 and with the specimen 27 and the glass slide 26 on the target plate 22.

Figure 2:
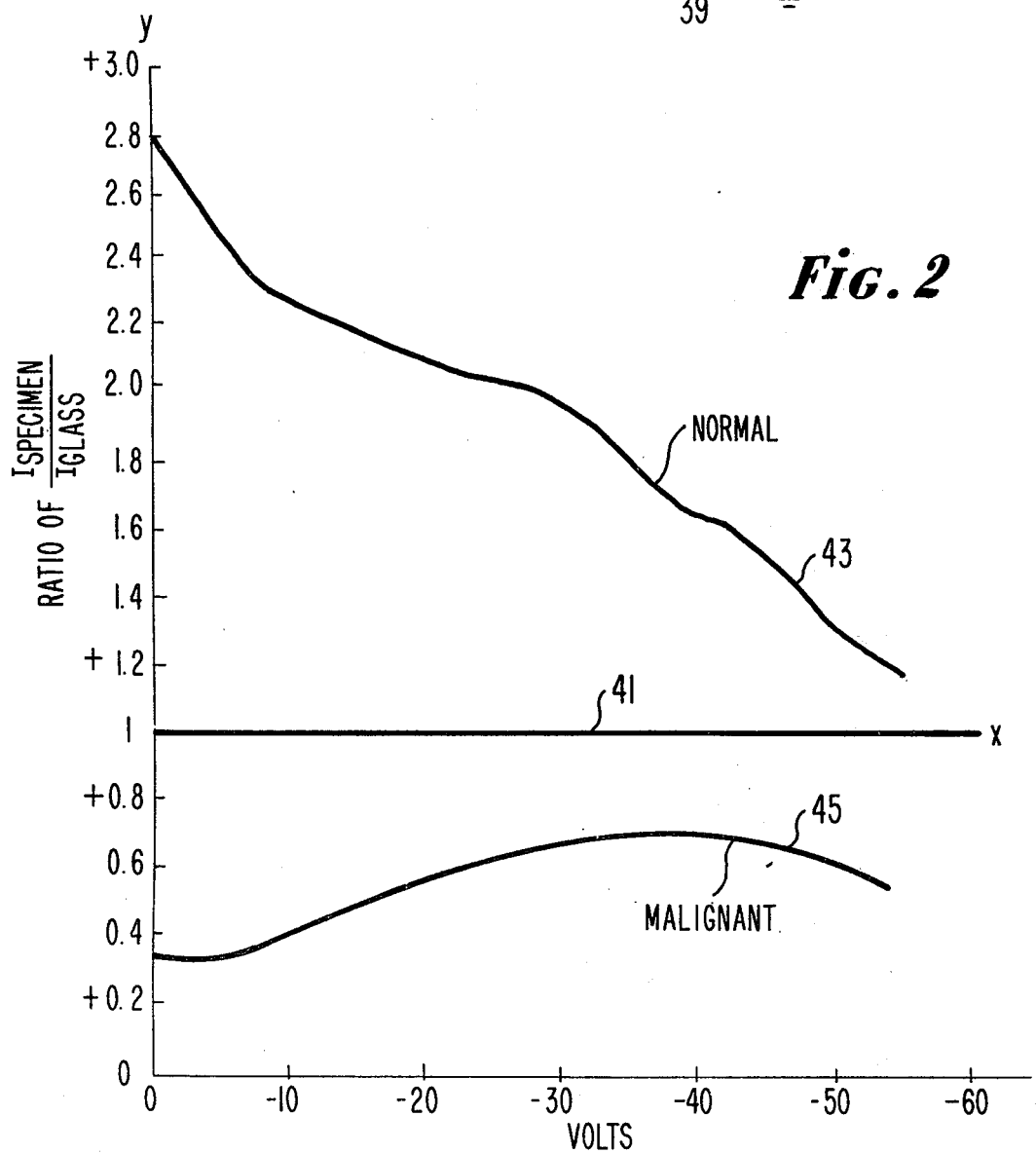
FIG. 2 is a plot of the ratio of measured current with specimen on a glass slide to measured current with glass slide only as a function of retardation bias voltage; and, FIG. 3 is a plot of the energy distribution of the secondary electrons vs. retardation bias voltage from normal and malignant specimens.
Figure 3:
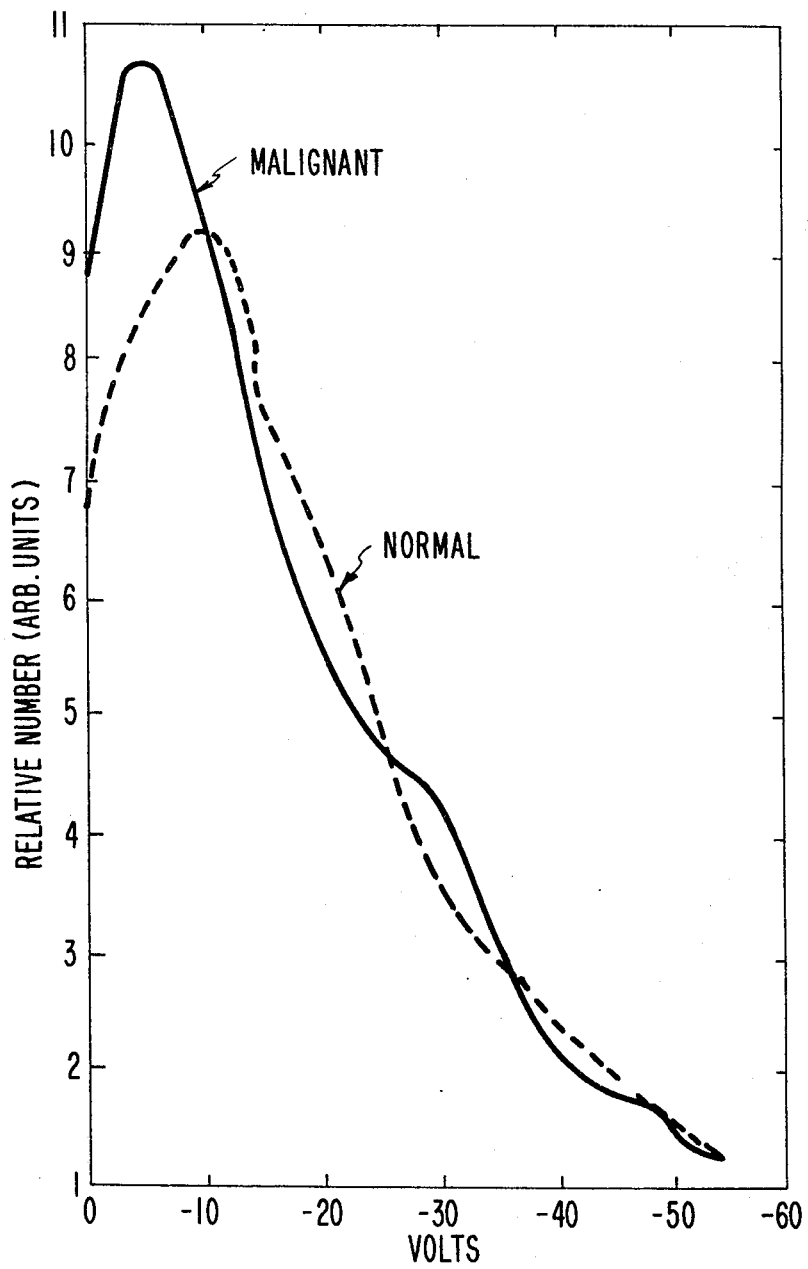

The curves shown in FIGS. 2 and 3 are based on data taken from tested samples according to the present invention. On the y-axis of FIG. 2, there is ploted the ratio of the measured current at electrometer 39 with the specimen on the glass slide divided by the measured current with glass slide only or y-axis = $I_{specimen}/I_{glass}$. The voltage on the x-axis of FIG. 2 is that of the net retardation potential on the dome 18. Specimens containing all normal cells show this ratio to be greater than one represented by line 41. Abnormal or malignant cells show a ratio less than 1. Curve 43 illustrates the value of 'specimen/'glass ratio for normal specimens to be between 2.8 and 1.2 for net negative retardation voltages from 0 to −55 volts applied to dome 18. Curve 45 illustrates that the value of 'specimen/'glass ratio for malignant specimens to be between +0.3 and +0.6 for the same net voltages from 0 to −55 volts applied to dome 18. By numerical integration of the area under curve 43 to base line 41 and of the area above curve 45 to base line 41, magnitudes are obtainable. Such magnitudes above curve 45 to base line 41 may be indicative of the extent of the malignancy.

FIG. 3 illustrates a plot of the relative energy distribution associated with the number of secondary electrons emitted (as measured by the current in the electrometer 39) as a function of the net retardation voltage from sources 31 and 33. Specimens containing malignant cells exhibited a maximum energy distribution (maximum number of secondary electrons emitted from the specimen) at about −5 volts, while specimens containing normal cells exhibited a maximum energy distribution at about −10 to −15 volts. Also the shape of the curve for malignant cells was more structured (deviated from smoothness).

Samples from 28 patients were examined. Under the "Pap" test, seventeen were found to be normal and eleven were found to be malignant. A biopsy was taken of five of the 11 and they were proven malignant. Samples from the same 28 patients were examined using the above described secondary electron emission technique. Of the 28 samples tested, 16 were found to be normal and 12 were found to be malignant. The 12 included the 11 samples found to be malignant by the "Pap" test, and one additional sample.

What is claimed is:

1. A method of analyzing a specimen of biological cells for malignancy comprising the steps of:
   exposing a specimen of biological cells to an electron beam, and
   measuring the secondary electron emission energy emitted from said specimen when exposed to said electron beam.

2. The method claimed in claim 1 wherein said electron beam is of sufficient magnitude to minimize noise due to the mixing of reflected primary electrons with emitted secondary emission electrons.

3. The method claimed in claim 1 wherein said electron beam acceleration potential is at least 50 volts.

4. The method claimed in claim 1 wherein said electron beam acceleration potential is less than that required to penetrate the specimen.

5. The method claimed in claim 4 wherein said electron beam acceleration potential is no greater than 10,000 volts.

6. The method claimed in claim 1 wherein said measuring step includes comparing secondary electrons emitted from said specimen on a glass slide to that emitted from the glass slide alone.

7. The method claimed in claim 1 wherein said measuring step includes applying a retardation potential near the specimen and determining the number of secondary electrons emitted as a function of retardation potential.

8. A malignancy detecting apparatus for analyzing a specimen of biological cells comprising:
   means for applying an electron beam to said specimen,
   means for measuring the secondary electron emissions from said specimen when exposed to said electron beam.

9. The combination claimed in claim 8 wherein said means for measuring includes an electron retardation system and a collection plate for secondary emission electrons and means for applying bias potentials to said plate and said system.

* * * * *